Figure 1:
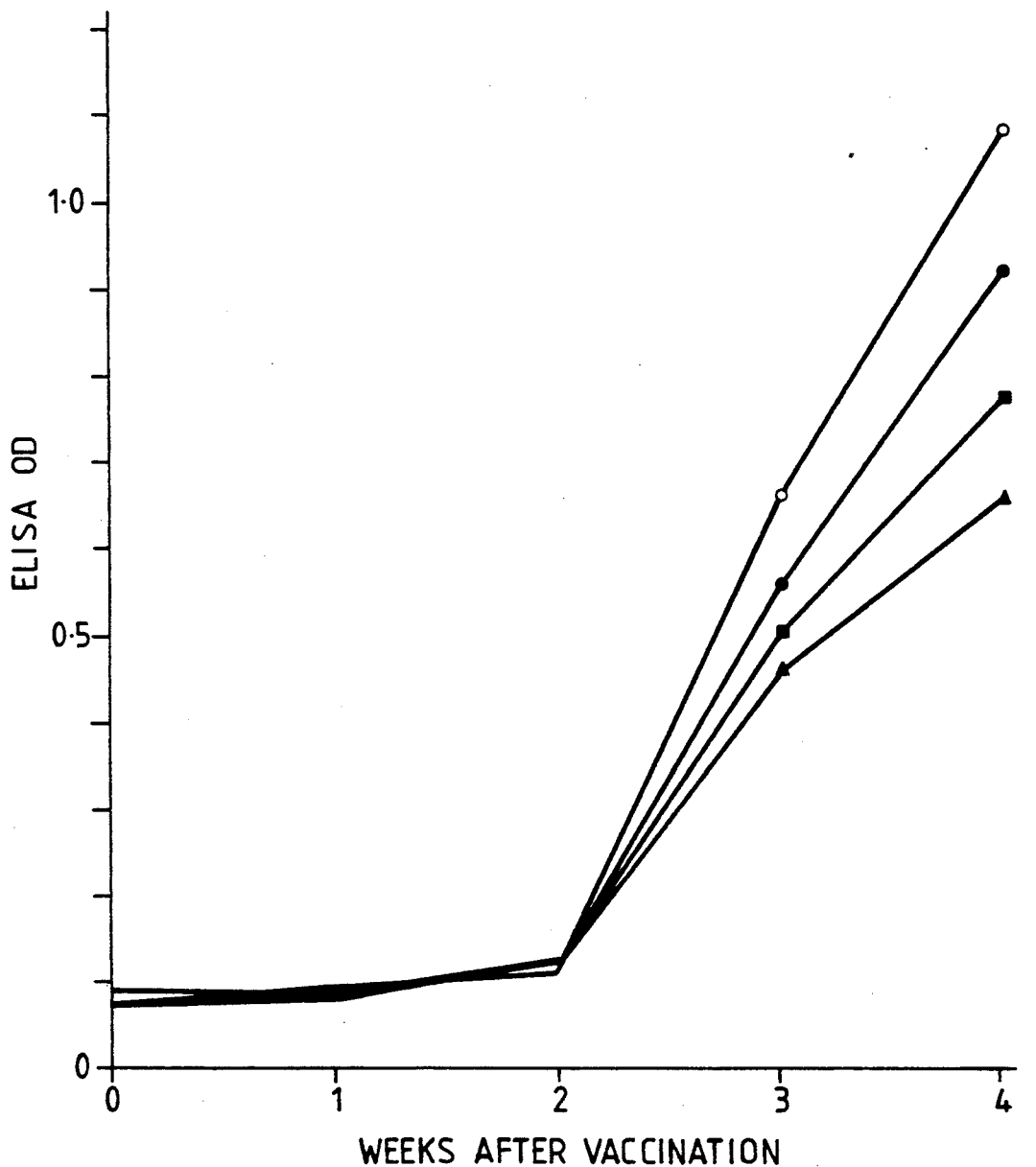

United States Patent [19]

Nicholas et al.

[11] Patent Number: 5,208,023

[45] Date of Patent: May 4, 1993

[54] VACCINE AGAINST AVIAN ENCEPHALOMYELITIS

[75] Inventors: Robin A. J. Nicholas, Farnham; Denise H. Thornton, Bagshot; Roy D. Goddard, Woodham, all of Great Britain

[73] Assignee: Minister of Agriculture, Fisheries & Food in Majesty's Government of Great Britain, London, England

[21] Appl. No.: 420,251

[22] Filed: Oct. 12, 1989

[30] Foreign Application Priority Data

Aug. 16, 1989 [GB] United Kingdom ............... 8918689

[51] Int. Cl.$^5$ .................... A61K 39/12; C12N 7/00
[52] U.S. Cl. ........................... 424/89; 424/88; 435/235.1; 435/236; 435/237; 435/239; 435/70.1; 435/245
[58] Field of Search .............. 424/89, 88; 435/235.1, 435/236, 237, 239, 70.1, 245

[56] References Cited

PUBLICATIONS

Bennjean et al., *Biological Abstracts*, vol. 63, (2), Ref. No. 9254, 1976.
Nicholas et al., *Research in Veterinary Science*, vol. 40, pp. 118-122, 1986.
Nicholas et al., *Arch. Virol.*, vol. 96, pp. 283-287, 1987.
Nicholas et al., *Biological Abstracts*, vol. 82 (1), Ref. No. 4932, 1986.
Nicholas et al., *Biological Abstracts*, vol. 85 (2), Ref. No. 22926, 1987.

*Primary Examiner*—Michael G. Wityshyn
*Assistant Examiner*—Abdel A. Mohamed
*Attorney, Agent, or Firm*—Nixon & Vanderhye

[57] ABSTRACT

A process for preparation of an attenuated strain of avian encephalomyelitis virus ("AEV") which may be used as a component of a protective vaccine, which comprises the steps of infecting chick embryo fibroblast ("CEF") cells with AEV, culturing the AEV-infected CEF cells until the AEV has become adapted to the CEF cells and then isolating the AEV product from the CEF cells for use in the vaccine. An attenuated AEV strain produced in this way, and tests showing use as a vaccine in chickens are also described.

20 Claims, 2 Drawing Sheets

GROWTH CURVE OF VR 25/15

VACCINE AGAINST AVIAN ENCEPHALOMYELITIS

This invention relates to a vaccine against avian encephalomyelitis (abbreviated herein to "AE"), and to a method of production thereof.

Avian encephalomyelitis virus (abbreviated herein to "AEV"), first described in 1932 causes the infectious disease AE in poultry, such as chicken, pheasants, turkeys, quails etc. In younger birds the disease is characterised by tremors of the head and neck, paralysis and death, whilst in older birds infection is subclinical and may cause a drop in egg production in laying flocks. The disease is therefore of considerable concern to poultry breeders and egg-producers.

AEV has been classified as an enterovirus of the family Picornaviridae. All reported isolates and vaccine strains are serologically identical to the prototype Van Roekel strain (Ref 1). Strains of this virus are publically available for example from Wellcome Laboratories, UK, or may be isolated from infected birds.

Vaccines against AE are known. These use the established technique of administration of attenuated strains of AEV. A disadvantage of currently used strains is that they are composed of chick embryo homogenate infected with mildly virulent strains of AEV. If administered to chicks or birds in production these strains often have the same effect as the disease itself (Ref 2). and may infect susceptible birds. Therefore present administration methods need to be very carefully controlled.

As a result birds can only be vaccinated when they have developed age resistance after about 10 weeks and at least a month before they come into lay.

Ref 3 describes a strain of AEV which has been replicated in chick embryo neuroglial ("CEN") cells, and in the process described therein has become adapted to CEN cells. In essence the process of Ref 3 involved serial passage up to 20 times through successive cultures of CEN cells. Replicated in this way the AEV was found to have some cell killing effect but only slight. CEN cells are however difficult to grow, requiring 8 days growth and a number of media changes before they can be infected, and they are consequently of essentially experimental interest only.

Consequently because of the problems outlined above there is a need for a safer AE vaccine. The invention seeks to achieve this by a novel process which results in a novel strain of attenuated AEV which retains antigenic similarity with the virulent infective virus, immunogenicity and stability. Other objects and advantages of the invention will be apparent from the following description.

According to this invention a process for preparation of an attenuated strain of AEV comprises the steps of:
a. infecting chick embryo fibroblast ("CEF") cells with AEV, then
b. culturing the infected CEF cells until the AEV has become adapted to CEF cells, then
c. isolating the AEV from the cultured CEF cells.

The process may be carried out starting with any available AEV strain. Preferably for vaccine purposes the strain used is serologically identical to the virulent prototype Van Roekel strain of AEV referred to above. Suitable strains include for example the publically available strain mentioned above (which is also available from Central Veterinary Laboratory, New Haw, Weybridge, Surrey, KT15 3NB, UK) and other known strains such as Calnek 1143, Hockstra 'HA' and AE-57.

The term "chick" as used herein refers generally to the young of all types of poultry or game birds, including chickens, turkeys, quails, ducks, geese, pheasants, pigeons etc unless otherwise specifically identified.

The CEF cells used in step (a) may be obtained by conventional procedures. Infection of the CEF cells may be by the conventional method of inoculating a culture of CEF cells in a suitable medium with an infective dose of the AEV strain. Preferably the CEF culture is at least 75% confluent at the time of infection.

It is however preferred to infect the CEF cells with an AEV strain which has previously been at least partly adapted to growth in embryonic cells, especially in embryonic brain cells, in particular in chick embryonic neuroglial brain ("CEN") cells (brain cells are about 80% CEN cells). Such cells may be obtained by conventional procedures, for example brain and/or CEN cells may be obtained by the method of Ref 4. The embryos from which CEN cells are obtained are preferably around 12, e.g. 10–15 days old. Adaptation of the AEV to such cells is preferably by infection followed by serial passage, and in brain, e.g. CEN, cells 5–35 levels of serial passage, preferably 20–30 e.g. 25, are generally suitable. An overall preferred method of adaptation of AEV to CEN cells, CEN cell type and CEN—adapted AEV strain are described in Ref 3.

Neither the CEF nor brain (e.g. CEN) cells need be obtained from the same type of bird for which an AE vaccine is required. For example cells from chicken embryos may be used to prepare an attenuated AEV strain which is suitable for use in a vaccine for chickens and other birds. In many countries however it is a legal requirement that cells which are used for producing vaccines are specific pathogen free ("SPF"). Chickens are among the few breeds of bird which are readily available in an SPF state, and consequently it is preferred that the CEF and brain or CEN (if used) cells which are used in the method of the invention are both obtained from SPF chicken embryos.

Infection of the CEF cells with the AEV which has been previously treated in this way may be by conventional methods. Generally a minimum of about 36 hours of incubation of AEV—infected brain, e.g. CEN, cells after initial infection is needed to produce an infective titre of CEN—associated AEV, i.e. found in both the culture medium as extra-cellular AEV and within the brain cells from whence it can be liberated by cell disruption, e.g. by sonication.

Adaptation of the AEV to CEF cells in the culturing step (b) is preferably achieved by serial passage through successive CEF cell cultures, and about 5–25 especially 10–20, conveniently 15 levels of passage, are usually necessary to achieve a suitable degree of adaptation of the AEV to the CEF cells.

Generally it is preferred to incubate the AEV-infected CEF cells for about 48–60 hours between passages as it is found that the titre of cell-associated virus reaches a maximum by this time.

An overall preferred methodology of adaptation of AEV to CEF cells is therefore to infect the CEF cells, incubate them (e.g. at 38.4° C.) for 48–72 hours, sonicate the cells to disrupt them and liberate intra-cellular AEV, then combine the sonicate and culture medium, and use this material to infect a fresh culture of CEF cells. This procedure is then repeated for the number of passage cycles used.

After this stage of serial passage the AEV is preferably cloned in CEF cells by the known technique of limiting dilution. This is conveniently achieved by growing the CEF cells in wells in microtitre plates, then diluting so as to give a single fluorescent foci in the microwells when subjected to the known fluorescent antibody test ("FAT") as described in refs 4 and 5. Where this occurs the culture fluid from a single well is collected, subcultured in fresh CEF cells and subject to further clonings. The purpose of this cloning stage is to attempt to ensure as far as possible that the AEV does not revert to a virulent strain. For use in vaccine purposes the legal requirements of some countries specify that a virus strain be subjected to a minimum of 3 clonings, and therefore the AEV is preferably cloned 3 or more times in this way.

The CEF cell-associated AEV may then be isolated in step (c) from the culture as extracellular AEV from the supernatant and/or via disruption of the CEF cells, e.g. by sonication, to liberate intra-cellular AEV, in either case the virus being physically separated from cells and/or cell debris. Known standard methods may be used to achieve this physical separation. The AEV may then be stored in suspension in a conventional manner. Alternatively the AEV may be lyophilised, preferably at a reduced temperature such as $-70°$ C., by conventional process, preferably in the presence of stabilisers such as lysine.

The CEF-associated AEV produced in this way is an attenuated strain that can be used as, or as a component of, a vaccine as it possesses the desirable characteristics of safety, effective protection, immunogenicity and the requirement for use of only a small dose to achieve protection. Moreover the strain appears to be purer than strains currently used for vaccine production. The CEF cells used in the process are relatively easy to culture on a scale that is convenient for commercial veterinary use. Further the attenuated AEV grows to about $10^5-10^6$ tissue culture median infective doses ("TCID50") per ml in CEF cell cultures, a level suitable for vaccine production as an economic venture in a process that promises to be a lot less labour intensive than currently used manufacturing processes. Furthermore the attenuated strain prepared in this way does not appear to do any harm if it spreads by infection to other birds, and can be transmitted in this way.

The attenuated AEV strain produced as a product by the process described above, being an AEV strain adapted to CEF cells, as itself a further aspect of the invention. A specimen of such an attenuated strain of AEV is deposited as Deposit No. V 89 091301 dated Sep. 13, 1989 at The European Collection of Animal Cell Cultures, Division of Biologics, PHLS/CAMR, Porton Down, Salisbury, Wilts SP4 OJG, United Kingdom, and the invention includes this strain, and mutations thereof or strains derived therefrom whether naturally evolving or produced by mutagenic treatment of said strain, provided such mutations and derived strains have attenuated virulence and have immunogenic effect.

The invention furthermore includes the use of an attenuated AEV strain produced as above as a vaccine, or as a component of a vaccine, against AE, and also includes an AE vaccine which contains as a component such an attenuated AEV strain.

When used as a vaccine or as a component of a vaccine, the AEV strain may be made up with other components conventional to the art, for example sterile water, buffers etc, to maintain the viability of the virus. The vaccine may also contain other attenuated virus strains, microorganisms, antigens etc so as to provide a vaccine which protects the inoculated birds against other diseases such as fowl pox, as well as AE. Methods of producing such multi-effect vaccines are known. Conveniently the vaccine may be provided in a pre-packaged form in quantities sufficient for a protective dose for a single bird or for a pre-specified number of birds, for example in sealed ampoules, capsules or cartridges for hypodermic syringes etc.

To achieve a degree of protection, at least for chickens, which is acceptable by United Kingdom standards, a dose of vaccine may contain as little as $10^{1.5}$ TCID 50 per bird by the preferred methods of inoculation. For protection to a higher standard preferably $10^{2.5}$ TCID 50 is administered per bird. A convenient maximum dose appears to be $10^{3.5}$ TCID 50 per bird as no increase in the degree of protection appears to be gained by increasing the dose above this. When administered by injection the vaccine should be contained in a volume of liquid which is appropriate for injection into the bird in question, as will be understood by those skilled in the art. Vaccine prepared and used in this way is suitable for inoculation of all birds which are susceptible to AE, but is of particular value for treatment of commercially bred poultry or game birds such as chickens, turkeys, quails, ducks, geese, pheasants, pigeons etc. The vaccine may be inoculated into birds to be protected by methods conventional to the art, such as orally (e.g. in drinking water) or via intra-muscular injection (e.g. by "wing stab").

The age at which the vaccine is administered to the birds to be protected will depend upon the type of bird and the purpose for which they are being kept, as will be understood by those skilled in the art. For example if the birds are being kept for meat production, it is preferable to inoculate them whilst they are still young, but if they are being bred for egg production it is preferable to inoculate them shortly before they are about to lay (for example with a "booster" dose) so that maternal antibodies may be transmitted to the young.

The invention will now be described by way of example only with reference to:

FIG. 1 which shows the immune response of groups of chicks to the attenuated AEV strain given by various routes.

Figure 2:
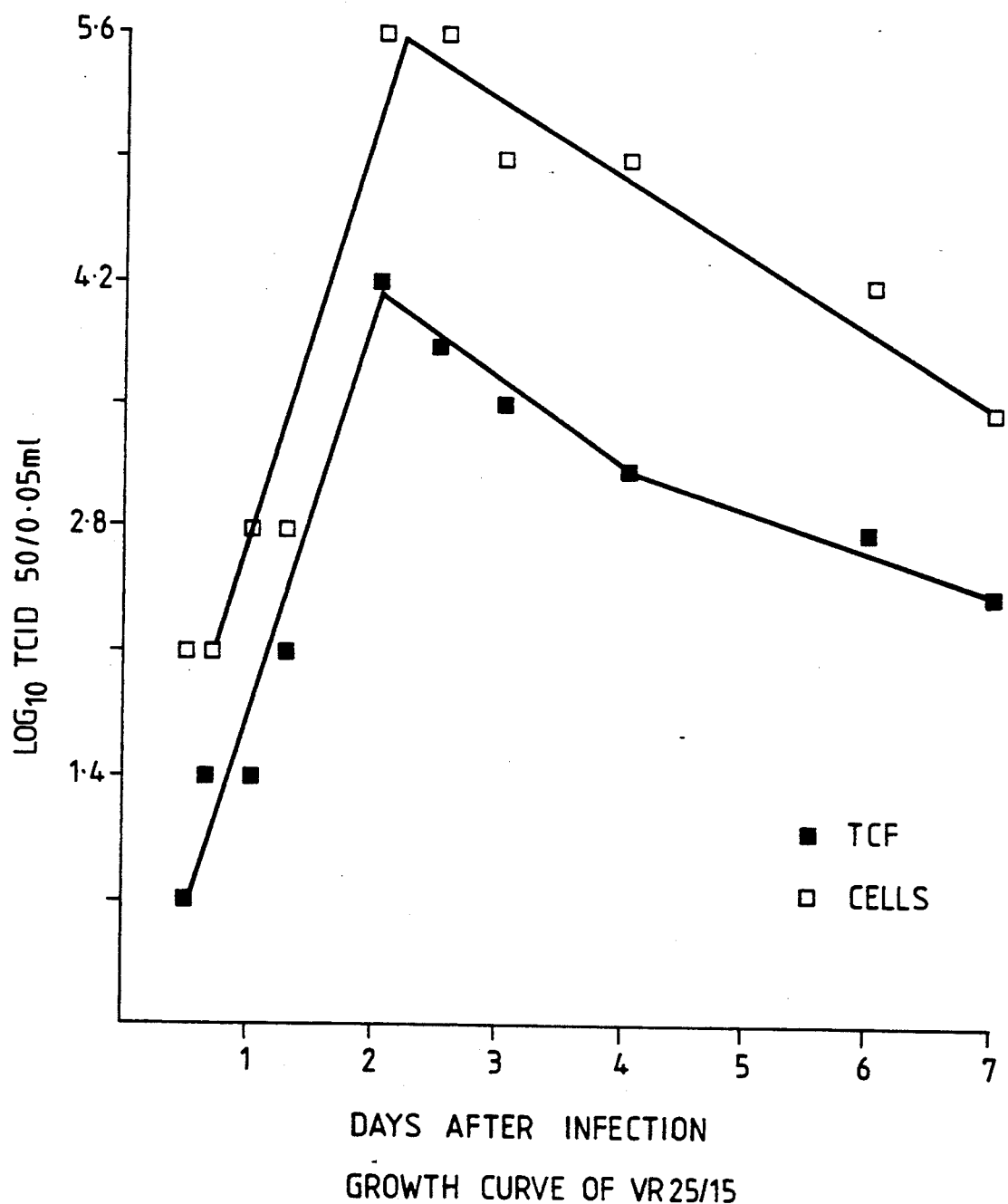

FIG. 2 which shows the rate of growth of a CEN-adapted AEV strain in CEF cells.

1. Tissue Culture Depositions

A deposit of the VR 25/15 virus referred to in the experimental examples below was made under the terms of the Budapest Treaty at The European Collection of Animal Cell Cultures, Division of Biologics, PHLS/CAMR, Porton Down, Salisbury, Wilts. SP4 OJG, United Kingdom on Sep. 13, 1989 as Deposit No. V 89 091301.

2. Virus

The history of the Van Rocckel strain of AEV used in this work has been described (Ref 3). 1 ml of $10^3$ TCID 50 doses of this strain was inoculated onto 50 ml flasks containing $10^6$ cells/ml of primary chick embryo brain (CEN) cell cultures, prepared as described in Ref 4. The virus was absorbed for one hour on the cells before overlaying with Medium 199 containing 5% foetal calf serum.

After 7 days incubation at 38.5° C. the cells and culture fluids were harvested separately. The cells were sonicated by three bursts of 20 seconds on an MSE Ultrasonicator with an interval of 60 seconds between bursts. The lysate was then added to the culture fluids and mixed. From this first passage material, 1 ml was inoculated onto freshly prepared brain cells, absorbed and overlaid. This fresh culture was again incubated, harvested, sonicated etc and inoculated into a fresh culture of brain cells as above. This procedure was repeated for a total of 25 passges. The sonicate from the 25 passages in brain cells was stored at −70° C.

1 ml of the above sonicate was inoculated onto 50 ml flasks containing $10^6$ cells/ml of chick embryo fibroblast (CEF) cells prepared by conventional procedures. The virus was absorbed for one hour before overlaying with Eagles MEM containing 5% foetal calf serum. After 3 days incubation at 38.5° C. the cells and culture medium were harvested separately, sonicated as above ($3 \times 20$ second bursts, 60 seconds between bursts). The lysate was then added to the culture fluids and mixed.

This mixture was inoculated onto freshly prepared CEF cells and the procedure was repeated. Subculturing in this manner was carried out for a total of 15 times. The sonicate from the 15 passages in CEF cells was stored at −70° C. It has a titre of $10^{5.8}$ TCID 50/ml as measured by the indirect immunofluorescence test.

The CEF sonicate was then subjected to cloning by limiting dilution. The virus was diluted in log steps across a microtitre plate containing CEF cells. After three days incubation the culture fluids were removed separately and an FAT carried out on the wells. Where a single fluorescent focus was seen in a microwell the culture fluid from that well was used and subcultured in CEF cells. This procedure was repeated on two occasions. The product was a cloned virus strain, referred to hereafter as VR 25/15.

For the production of vaccine seed material, primary CEF cells grown in roller culture bottles were infected with 1 ml of VR 25/15 containing $10^5$ TCID 50/ml. After one hours absorption the cells were overlaid with 100 ml of media and incubated for three days at 38.5° C. The cells and culture fluid were harvested separately, sonicated etc as above. The virus was aliquoted and stored at −70° C.

3. Serological Test and Immunogenicity

Antigen for the indirect enzyme-linked immunosorbent assay (ELISA) was prepared as described in Ref 6 and used at a dilution of 1/200. The procedure was essentially that of Goddard et al Ref 7 using 1/100 dilutions of sera unless otherwise stated.

For the indirect fluorescent antibody test (FAT) primary chick embryo fibroblast cell cultures, grown on multiwell slides, were infected with $10^{3.4}$ tissue culture median infective doses (TCID50) per well of VR 25/15. After 48 hours the cells were fixed in acetone and stored at −20° C. until required. The FAT was carried out as described in Ref 6 using 1/50 dilutions of antisera unless otherwise stated. To assess immunogenicity groups of 10 two week old SPF chicks were inoculated with 100 μl of VR 25/15—containing $10^{3.5}$ TCID50s by one of three routes: intramuscular, oral or intracerebral. A fourth group were kept as uninoculated controls. All groups were housed in separate isolators. Three uninoculated contact control birds were housed with each infected group. The birds were bled at weekly intervals for four weeks and the sera examined for antibodies to AEV by ELISA and FAT.

The results of the serological response of the different groups to the virus, measured by the ELISA, are shown in FIG. 1. The oral route was slightly higher after three weeks and significantly higher after 4 weeks. The contact control birds seroconverted rapidly reaching a higher level than those inoculated. No birds showed any signs of AE.

During this experiment, sera from the individual birds were monitored on a qualitative basis by ELISA and FAT. For the ELISA, a cut-off point differentiating positive and negative sera was established as described in Ref 6; this value was 0.15. Table 1 shows the results of the serological comparison. After two weeks 7 sera were positive by ELISA and 4 by FAT. After three weeks 21 sera were positive by ELISA and 23 by FAT. After four weeks all sera were positive by both tests. Good correlation was seen with both tests. To provide some quantitative assessment of sensitivity sera were pooled within groups bled at three and four weeks. The pooled sera were titrated in two fold steps by ELISA and FAT. Results are seen in table 2. The tests were of similar sensitivity.

TABLE 1

Comparison of ELISA and FAT

| Test | Days After Infection 7 | 14 | 21 | 28 |
|---|---|---|---|---|
| ELISA | 0 | 7 | 21 | 29 |
| FAT | 0 | 4 | 23 | 30 |

TABLE 2

Comparison of Titres of ELISA and FAT

| Route | Week 3 ELISA | Week 3 FAT | Week 4 ELISA | Week 4 FAT |
|---|---|---|---|---|
| Oral | 1/1600 | 1/1600 | 1/3200 | 1/600 |
| Intra-muscular | 1/800 | 1/800 | 1/3200 | 1/1600 |
| Intra-cerebral | 1/800 | 1/800 | 1/1600 | 1/1600 |
| Control | 1/200 | 1/200 | 1/6400 | 1/6400 |

4. Replication Characteristics in Cell Cultures

To determine the optimum time for harvesting of the virus for vaccine production, a growth study was initiated. Fifty ml culture bottles and multiwell slides were inoculated with 100 μl of neat stock virus containing 5.1 (log 10) TCID50/ml. At regular intervals after inoculation the slides were fixed in acetone and the FAT carried out as described in Ref. 3. At the same time the culture fluids and cells from two flasks were pooled. The cells were centrifuged at low speed and the culture fluids were tipped off and stored at −70° C. The cells were resuspended in 1 ml of phosphate buffered saline (PBS), freeze-thawed three times and stored at −70° C. The samples were titrated in microtitre by FAT.

Virus was first detected after 12 hours of infection and consisted of fine multiple granules scattered throughout the cytoplasm. By 48 hours the fluorescence had become very intense and had coalesced into granules usually located in a perinuclear position. By 72 hours small foci of infected cells were present. No nuclear fluorescence was seen throughout this experiment. No overt cytopathic effects were evident.

There was a linear increase in the amount of cell-associated virus from 6 to 48 hours reaching a peak of 5.6 (log 10) TCID 50s/50 μl. From 60 hours onwards the titre gradually declined to 3.5 after 7 days. The increase in extracellular virus paralleled that in the cells reaching 4.2 after 48 hours and declining after that to 2.4 (FIG. 2).

5. Safety

Neat stock virus of the attenuated strain was inoculated intracerebrally into 10 two week old SPF chickens using 100 μl of inoculum/bird. The birds, housed in isolators, were observed daily for three weeks for clinical signs such as ataxia, incoordination or tremors of the head and neck. The same amount of virus was also inoculated into the yolk sac of 25 five day old SPF chick embryos. The embryos were incubated for 14 days at 38.5° C. After this time the embryos were examined for signs of AEV such as stunting and limb deformities. Brain material from these embryos was pooled and inoculated into a further group of five day old embryos. This was repeated on one further occasion.

None of the birds inoculated intracerebrally showed any sings of AE during the three week observation period. Similarly none of the embryos from any passage level died or showed signs attributable to AEV. Virus could be recovered from the brains of infected embryos at each passage level.

6. Minimum Protective Dose

Groups of 10 two week old chicks were each inoculated orally with 3.5, 2.5 or 1.5 TCID 50s/bird. A fourth group was kept as unvaccinated controls. After three weeks all birds were challenged with $10^3$ TCID 50s of virulent Van Roekel AEV intra-cerebrally. For the next three weeks the birds were observed daily for signs attributable to AEV.

ELISA values recorded three weeks after vaccination and just before challenge, were high in all vaccinated birds; unvaccinated birds had very low values. All vaccinated birds were protected from challenge even at the $10^{1.5}$ dose level. Unvaccinated birds began to show clinical signs of AE 7 days after challenge (table 3).

TABLE 3

| Minimum Protective Dose | | |
|---|---|---|
| Dose (Log 10 TCID50) | ELISA OD | No. of birds showing AE |
| 3.5 | 1.24 | 0/10 |
| 2.5 | 0.82 | 0/10 |
| 1.5 | 0.86 | 1/10 |
| control | 0.02 | 7/10 |

7. Discussion of Experimental Results

The experiments described above indicate that the attenuated strain of AEV obtained by culture of the AEV in CEF cells has many advantages over the vaccine strains licensed for use in the UK at present. Primarily the strain was safe by all routes in chicks even by intracerebral route. Of the five commercial vaccine strains from six manufacturers examined by Bennejean et al (Ref 2) all were pathogenic at the recommended dose and route in 1, 7 and 14 day old chicks. Further evidence of innocuity of VR25/15 is seen in embryos where no signs of AEV were recorded although virus was easily recoverable.

The above experiments indicate that the attenuated strain VR 25/15 showed good immunogenicity by all three routes used, particularly the oral route which is that recommended for commercial vaccination. Furthermore the immune response of the contact control birds was impressive, demonstrating that inadequately vaccinated birds would be protected very rapidly by contact. None of the contact control birds showed clinical evidence of AE which suggests that inadvertant viral spread would have little effect on susceptible birds.

In the minimum protective dose experiment all groups down to 1.5 (log10) TCID50/bird were protected against challenge. The ELISA values of the vaccinated birds, taken at three weeks post vaccination, easily satisfied the criterion of the UK Control Authority's draft guidelines. These state that 80% of the vaccinates shall contain antibody to AEV and that the mean value shall be at least three times that of the unvaccinated controls.

With the vaccine growing to about 6.0 (log 10) TCID50/ml in cell culture and the minimum protective dose as low as 1.5 (log 10) TCID50/bird it would seem that vaccine production is an economic venture. The product would also be somewhat purer and certainly less labour-intensive to manufacture.

Data was also provided on the relative efficiencies of two serological tests: the indirect ELISA and FAT. The ELISA appeared to detect positive sera a little earlier than the FAT but generally there was excellent correlation. In laboratories geared to immunoassay techniques the ELISA would be the test of choice but in less well equipped laboratories the FAT provides a cheap, robust and less equivocal method of antibody detection.

References

1. Luginbuhl R E, Helmboldt C F, (1972) Avian Encepholomyelitis. In Hofstadt M S (ed) Diseases of Poultry, 6th Edn., The Iowa State University Press, Ames, Iowa, 657–669.
2. Bennejean G, Picault J P, Lahellec M, Guittet M, (1976). Study of the properties of different strains of avian encepholomyelitis virs, Folia Vet Lot 6, 179–188.
3. Nicholas R A J, Ream A J, Thornton D H, (1987) Archives of Virology, Replication of avian encepholomyelitis virus in chick embryo neuroglial cultures, 96, 283–287.
4. Nicholas R A J, Wood G W, Hopkins I G, Thornton D H, (1986), Detection of avian encephalomyelitis. Res Vet Sci 40, 118–120.
5. Berger R G, (1982), An in vitro assay for quantifying the virus of avian encephalomyelitis. Avian Dis 26, 534–541.
6. Nicholas R A J, Goddard R D, Ream A J, Hopkins I G, Thornton D H (1986), Improved potency test for live avian encephalomyelitis vaccines. Res Vet Sci 41, 420–422.
7. Goddard R D, Nicholas R A J, Luff P R, (1988) Serology-based potency test for inactivated Newcastle Disease vaccines. Vaccine 6, 530–532.

We claim:

1. A process for preparation of an attenuated strain of avian encephalomyelitis virus ("AEV") which comprises the steps of:
   a. infecting chick embryo fibroblast ("CEF") cells with AEV, then b. culturing the infected CEF cells until the AEV has become adapted to the CEF cells, then c. isolating the AEV from the cultured CEF cells.

2. A process according to claim 1 wherein the AEV strain used to infect the CEF cells in step a. has previously been at least partly adapted to chick embryonic brain cells.

3. A process according to claim 2 wherein the brain cells are chick embryonic neuroglial ("CEN") cells.

4. A process according to claim 1 wherein the CEF cells are produced from the embryos of chickens.

5. A process according to claim 3 wherein the CEF and CEN cells are both produced from the embryos of chickens.

6. A process according to claim 5 wherein the AEV is adapted to CEN cells by 5-35 levels of serial passage of the AEV through CEN cells.

7. A process according to claim 6 wherein the AEV is adapted to CEN cells by 25 levels of serial passage of the AEV through CEN cells.

8. A process according to claim 5 wherein the adaptation of the AEV to CEF cells is achieved by 10-20 levels of serial passage of the AEV through CEN cells.

9. A process according to claim 8 wherein the AEV is adapted to CEF cells by 15 levels of serial passage of the AEV through CEN cells.

10. A process according to claim 8 wherein the infected CEF cells are incubated for 48-60 hours between passages.

11. A process according to claim 8 wherein subsequent to the serial passage the AEV is cloned in CEF cells.

12. A process according to claim 11 wherein the AEV is cloned by limiting dilution, then subcultured in fresh CEF cells and then subjected to two further clonings.

13. An attenuated strain of AEV, adapted to CEF cells, produced by the process as claimed in claim 1

14. An attenuated strain of AEV which has been subjected to the following process:
a. 5-30 times of serial passage of the AEV through CEN cells from chicken embryos,
b. 10-20 times of serial passage of the AEV from step a through CEF cells from chicken embryos, and
c. isolation of the AEV from the cultured GEF cells.

15. An attenuated strain of AEV according to claim 14 wherein serial passage in a. is 25 times and in b. is 15 times.

16. An attenuated strain of AEV according to claim 15 which is deposited at The European Collection of Animal Cell Cultures Division of Biologics, designated with an accession number No. X 89 091301.

17. A vaccine against AE which comprises as a component an attenuated strain of AEV as claimed in claim 13 together with a vaccine carrier.

18. A vaccine against AE which comprises as a component an attenuated strain of AEV as claimed in any one of claims 14 to 16 and a vaccine carrier.

19. A vaccine according to claim 18 when in a prepackaged form comprising a sufficient quantity of the strain for a protective dose for a single bird or a prespecified number of birds, each dose being between $10^{1.5}$ to $10^{3.5}$ TCID50 per bird, and a vaccine carrier.

20. A vaccine according to claim 19 wherein the quantity is $10^{2.5}$ and $10^{3.5}$ TCID50 per bird.

* * * * *